US011304724B2

(12) United States Patent
Kilemnik

(10) Patent No.: US 11,304,724 B2
(45) Date of Patent: Apr. 19, 2022

(54) INCISING IMPLANT FOR THE PROSTATIC URETHRA

(71) Applicant: MEDI-TATE LTD., Or Akiva (IL)

(72) Inventor: Ido Kilemnik, Haniel (IL)

(73) Assignee: MEDI-TATE LTD., Or Akiva (IL)

( * ) Notice: Subject to any disclaimer, the term of this patent is extended or adjusted under 35 U.S.C. 154(b) by 258 days.

(21) Appl. No.: 15/109,311

(22) PCT Filed: Dec. 2, 2014

(86) PCT No.: PCT/IL2014/051045
§ 371 (c)(1),
(2) Date: Jun. 30, 2016

(87) PCT Pub. No.: WO2015/101975
PCT Pub. Date: Jul. 9, 2015

(65) Prior Publication Data
US 2016/0317180 A1    Nov. 3, 2016

Related U.S. Application Data

(60) Provisional application No. 61/921,590, filed on Dec. 30, 2013, provisional application No. 62/077,331, filed on Nov. 10, 2014.

(30) Foreign Application Priority Data

Nov. 23, 2014    (WO) .................. PCT/IL2014/051015

(51) Int. Cl.
*A61B 17/3209* (2006.01)
*A61F 2/04* (2013.01)
(Continued)

(52) U.S. Cl.
CPC ............ *A61B 17/3209* (2013.01); *A61F 2/04* (2013.01); *A61B 17/320725* (2013.01);
(Continued)

(58) Field of Classification Search
CPC .......... A61F 2002/016; A61F 2002/047; A61F 2/04; A61F 2/82; A61F 2/848; A61F 2/86;
(Continued)

(56) References Cited

U.S. PATENT DOCUMENTS 5,269,802 A    12/1993  Garber
7,806,888 B2   10/2010  Frassica
(Continued)

FOREIGN PATENT DOCUMENTS

RU    2062121 C1    6/1996
RU    2429804 C2    9/2011
(Continued)

OTHER PUBLICATIONS

Search Report for European Patent Application No. 14877420.1, dated Aug. 3, 2017.
(Continued)

*Primary Examiner* — Sarah W Aleman
(74) *Attorney, Agent, or Firm* — Merchant & Gould P.C.

(57) ABSTRACT

An incising implant for creating incisions in the prostatic urethra of a subject, the implant including at least two closed-shaped wires, each of the wires having a proximal section, a distal section and two longitudinal sections extending between the proximal section and the distal section, each of the closed-shaped wires being elastic thereby being compressible into a compressed configuration, each of the longitudinal sections of each of the wires being adjoined with another longitudinal section of another one of the wires.

16 Claims, 5 Drawing Sheets

(51) Int. Cl.
  *A61B 17/00*     (2006.01)
  *A61B 17/3207*   (2006.01)

(52) U.S. Cl.
  CPC ............ *A61B 2017/00274* (2013.01); *A61B 2017/00862* (2013.01); *A61B 2017/32096* (2013.01); *A61B 2017/320733* (2013.01); *A61F 2002/047* (2013.01)

(58) Field of Classification Search
  CPC ............ A61F 2/94; A61F 2002/821; A61F 2002/825; A61F 9/007; A61F 9/00781; A61B 2017/2215; A61B 17/0057; A61B 17/22031; A61B 17/221; A61B 17/32056; A61B 17/32096
  See application file for complete search history.

(56) References Cited

U.S. PATENT DOCUMENTS

| | | | | |
|---|---|---|---|---|
| 2003/0023265 A1* | 1/2003 | Forber | ............ | A61F 2/013 606/200 |
| 2003/0040771 A1* | 2/2003 | Hyodoh | ............ | D04C 1/06 606/200 |
| 2004/0059373 A1* | 3/2004 | Shapiro | ............ | A61F 2/01 606/200 |
| 2005/0165441 A1* | 7/2005 | McGuckin, Jr. | ............ | A61F 2/01 606/200 |
| 2006/0241675 A1 | 10/2006 | Johnson et al. | | |
| 2008/0086149 A1* | 4/2008 | Diamant | ............ | A61B 17/221 606/113 |
| 2009/0069828 A1* | 3/2009 | Martin | ............ | A61B 17/221 606/159 |
| 2010/0137893 A1 | 6/2010 | Kilemnick et al. | | |
| 2011/0276081 A1* | 11/2011 | Kilemnik | ............ | A61F 2/94 606/198 |
| 2013/0184738 A1 | 7/2013 | Laroya | | |
| 2013/0184741 A1 | 7/2013 | Laroya et al. | | |

FOREIGN PATENT DOCUMENTS

| | | |
|---|---|---|
| WO | 2006/040767 A1 | 4/2006 |
| WO | 2007/062661 A2 | 6/2007 |

OTHER PUBLICATIONS

International Search Report and Written Opinion for PCT/IL2014/051045, dated Jun. 3, 2015.

\* cited by examiner

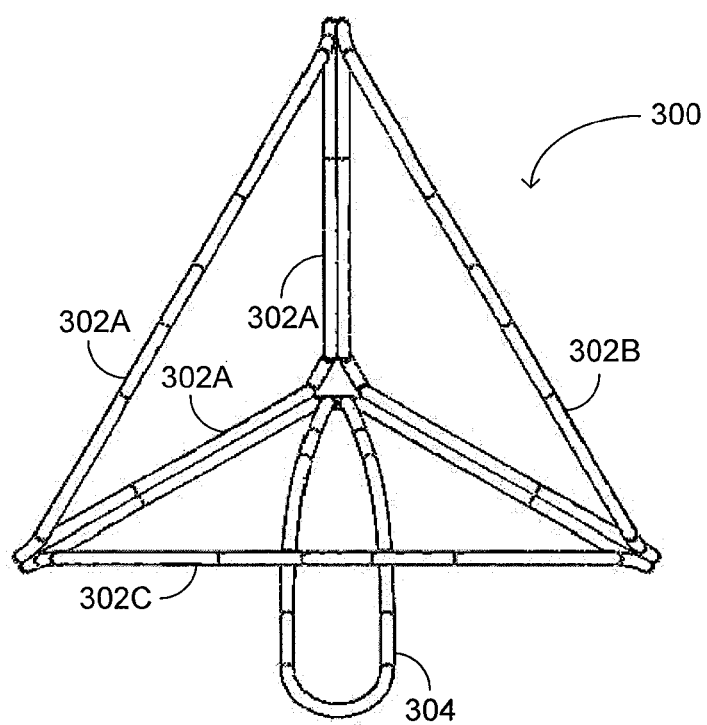
FIG. 3
FIG. 4A  FIG. 4B

INCISING IMPLANT FOR THE PROSTATIC URETHRA

This application is a National Stage Application of PCT/IL2014/051045, filed 2 Dec. 2014, which claims benefit of U.S. Ser. No. 61/921,590, filed 30 Dec. 2013, U.S. Ser. No. 62/077,331, filed 10 Nov. 2014, and claims priority to PCT/IL2014/051015, filed Nov. 23, 2014, which applications are incorporated herein by reference. To the extent appropriate, a claim of priority is made to each of the above disclosed applications.

FIELD OF THE DISCLOSED TECHNIQUE

The disclosed technique relates to systems and methods for relieving a prostate enlargement (e.g., as a result of benign prostatic hyperplasia). In general, and to systems and methods for creating incisions in the inner wall tissues of the prostatic urethra.

BACKGROUND OF THE DISCLOSED TECHNIQUE

The prostate is a walnut-sized gland that forms part of the male reproductive system. The prostate is located in front of the rectum and just below the bladder, where urine is stored. The prostate surrounds a portion of the urethra (hence referred to as the prostatic urethra), the canal through which urine passes out of the body. Prostate enlargement can result from a number of medical problems such as Benign Prostatic Hyperplasia (BPH), prostatic Bladder Neck Obstruction (BNO) and the like. The enlarged prostate applies pressure on the urethra (i.e., on the prostatic urethra and possibly on neighboring areas, such as the bladder neck and damages bladder function.

Infarction is a process resulting in a macroscopic area of necrotic tissue in some organ caused by loss of adequate blood supply. The inadequate blood supply can result from pressure applied to the blood vessels. Even by applying a relative small but continuous pressure on a tissue, one can block the tiny blood vessels within the tissue and induce infarction.

PCT Patent Application Publication No. WO 2006/04076 A1, to Kilemnik; and entitled "Prostate Treatment Stent" is directed at a tissue dissecting implant. The implant is spring-shaped and includes a plurality of rings elastically coupled therebetween. Adjacent rings apply pressure on tissues caught between the rings, thereby pinching the caught tissues and inducing necrosis.

US Patent Application Publication No. 2011/0276081 to Kilemnik, and entitled "Radial Cutter Implant" is directed at an implant for applying radial forces on the tissues surrounding it. The implant includes wires for applying radial pressure oh the surrounding tissues. Each of the wires extends in a different radial direction, and therefore, each wire applies pressure on different tissues. The implant can further include a longitudinal central tube, such that the wires are coupled with a proximal end and a distal end of the tube. The tube supports the wires and provides structural stability to the implant. The distal end of the wires is positioned within the bladder of the subject, and may irritate the bladder.

SUMMARY OF THE DISCLOSED TECHNIQUE

It is an object of the disclosed technique to provide methods and systems for implanting an incising implant in a prostatic urethra of a subject for creating longitudinal incisions in the inner walls of the prostatic urethra. In accordance with the disclosed technique, there is thus provided an incising implant for creating incisions in the prostatic urethra of a subject. The implant includes at least two closed-shaped wires. Each of the wires has a proximal section, a distal section and two longitudinal sections extending between the proximal section and the distal section. Each of the closed-shaped wires is elastic, and thereby compressible into a compressed configuration. Each of the longitudinal sections of each of the wires is adjoined with another longitudinal section of another one of the wires.

In accordance with another embodiment of the disclosed technique, there is thus provided a method for implanting an incising implant within a prostatic urethra of a subject. The method includes the steps of enfolding the incising implant within a sheath and inserting the sheath into a urethra of the subject. The incising implant is elastic. When the implant is enfolded within the sheath the implant is compressed such that the implant conforms to a diameter of the sheath. The sheath is inserted into the urethra until a distal end of the sheath extends into a bladder of the subject. The method further includes the steps of pushing the incising implant within the sheath until the incising implant exits the distal end of the sheath into the bladder, and pulling the incising implant until the incising implant is implanted within the prostatic urethra.

BRIEF DESCRIPTION OF THE DRAWINGS

The disclosed technique will be understood and appreciated more fully from the following derailed description taken in conjunction with the drawings in which:

FIG. 3 is a schematic illustration of an incising implant for creating incisions in the inner wall tissues of the prostatic urethra, constructed and operative in accordance with a further embodiment of the disclosed technique;

FIGS. 4A and 4B are schematic illustrations of a proximal niche of a proximal cap of an incising implant, constructed and operative in accordance with yet another embodiment of the disclosed technique.

DETAILED DESCRIPTION OF THE EMBODIMENTS

Figure 1A:
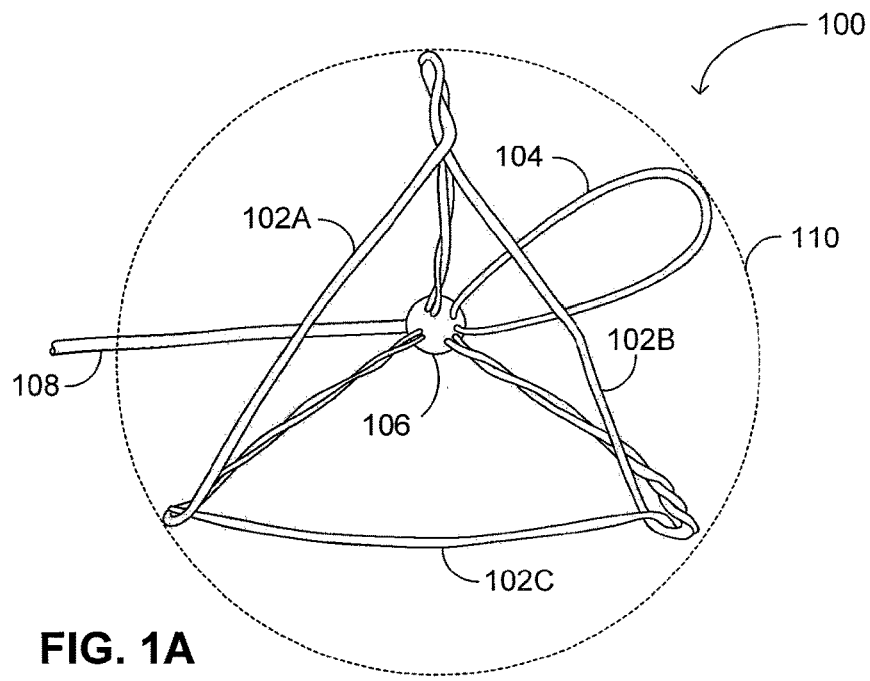
FIGS. 1B and 1C are schematic illustrations of an incising implant for creating incisions in the inner wall tissues of the prostatic urethra, constructed and operative in accordance with an embodiment of the disclosed technique.

The disclosed technique overcomes the disadvantages of the prior art by providing an incising implant to be implanted in the prostatic urethra (or at the vicinity thereof, for example, in the bladder neck). The incising implant includes wires which apply radial force on the surrounding inner wall tissues of the prostatic urethra. Over time, the wires induce infraction and thereby produce longitudinal incisions in the surrounding tissues. The incisions relieve constriction of the prostatic urethra.

In accordance with an embodiment of the disclosed technique, the incising implant is formed by three closed-shape wires (or more). The shape of each wire can be roughly divided into a proximal section, a distal end section and two longitudinal sections extending between the proximal and the distal sections. Each wire is made of an elastic material allowing it to be compressed into a sheath, and to assume its original shape when released from the sheath.

The longitudinal sections of each wire are adjoined with longitudinal sections of adjacent wires. Thereby, the wires are coupled to each other to form a frame of wires. Each wire forms a face of the wire frame, and the adjoined longitudinal sections form the edges of the wire frame. The edges of the wire frame apply radial pressure on the inner wall tissues of the prostatic urethra, thereby creating longitudinal incisions that relieve urethral constriction and increase the urinal passage.

The wires, when applying pressure on the surrounding tissues, are pressed against one another (i.e., each wire is pressed against adjacent wires to which it is adjoined at the respective longitudinal sections). Thereby, the wires support each other. In other words, when a wire applies a force on a tissue, the tissue applies an opposite force having the same magnitude (in accordance with Newton's third law). The wire is thus pressed against adjoined adjacent wires. These adjoined wires, in turn, are pushed against other tissues. In this manner, the wire frame is self-supporting, obviating the need for an additional supporting element, such as a central support tube. Additionally, each edge of the wire frame is formed by two adjoined wires, doubling the pressure applied on the tissues and allowing for thinner wires.

In accordance with another embodiment of the disclosed technique, there is thus provided a method for deploying an incising implant in the prostatic urethra of the subject. The method involves enfolding the incising implant within a sheath. The implant is elastic and thereby conforms to the circumference of the enfolding sheath which is smaller than the circumference of the implant. The sheath is inserted into the urethra and is pushed until its distal end extends into the bladder of the subject. The implant is pushed within the sheath until it extends from the distal end of the sheath. Once released from the sheath the elastic implant resumes its original, extended, configuration.

The implant can include a proximal cap having a proximal niche (or a proximal protrusion). The proximal niche is a non-round niche that can transfer rotary motion from a corresponding pin (or in case of a proximal protrusion—a corresponding niche). Thereby, the user can rotate the implant within the bladder to a desired rotary orientation.

Thereafter, the implant is pulled back in the proximal direction until it is positioned within the prostatic urethra (and/or the bladder neck). The implant remains within the prostatic urethra for a period of time (e.g., several hours or several day), during which the implant creates longitudinal incisions in the surrounding inner wall tissues of the urethra for relieving urethral constrictions. After the period of time passes, a sheath is inserted into the urethra and enfolds the implant, thereby compressing the implant back to a compressed configuration. Following this, the implant is removed from the urethra via the sheath.

The terms pressure and force (e.g., applying radial pressure or applying radial force) are employed interchangeably herein below, to describe the operation of the wires of the implant on the surrounding tissues. That is, the wires are described as applying pressure on the tissues, or as applying force on the tissues. Herein below, the terms proximal and distal refer to directions relative to implantable device and the delivery system. In particular, the distal end is the end of the device (or of the system) that is inserted into the body of the patient first and reaches the deepest. The proximal end is the end closer to the exit from the body of the patient.

Figure 1B:
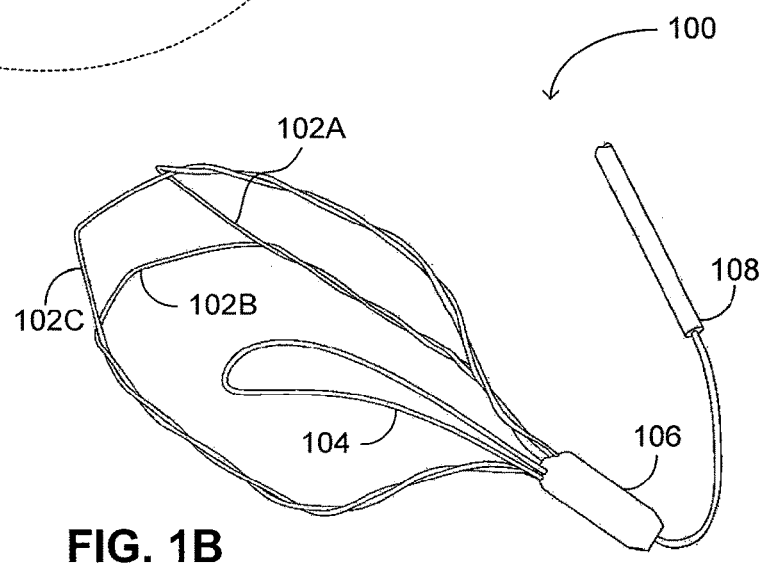
Figure 1C:
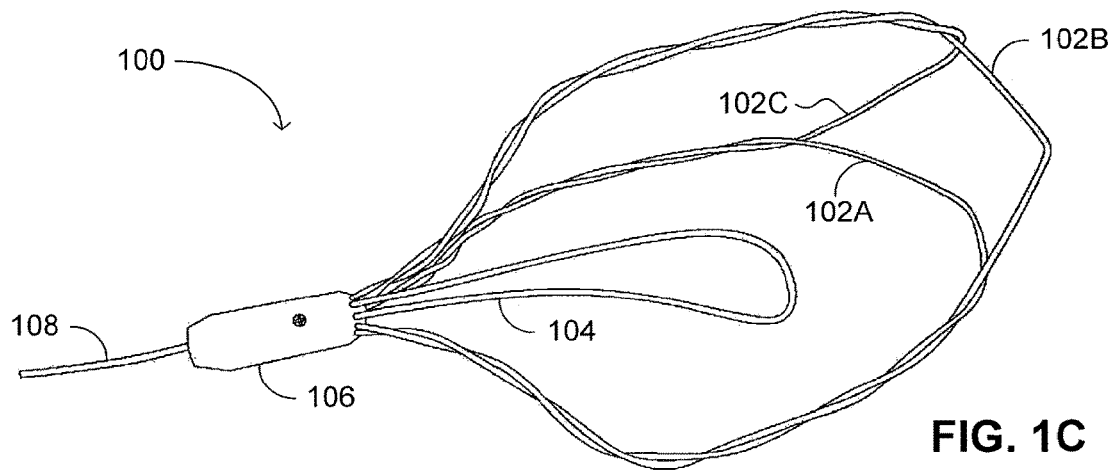

Reference is now made to FIGS. 1A, 1B and 1C, which are schematic illustrations of an incising implant, generally referenced 100, for creating incisions in the inner wall tissues of the prostatic urethra, constructed and operative in accordance with an embodiment of the disclosed technique. FIG. 1A depicts the incising implant from a top-view perspective (i.e., as would be seen in case the observer is located distally to the implant), and FIGS. 1B and 1C depict the incision implant from opposite isometric perspectives. Incising implant 100 Includes three closed-shaped wires 102A, 102B and 102C (also referred to herein below, together, as wires 102), an anchoring leaflet 104, a proximal cap 106, and an extraction string 108.

The closed shape of each of wires 102 can roughly be divided into a proximal section, a distal section and two longitudinal sections extending between the proximal section and the distal section. For example, the proximal section can be a U-shaped proximal end, from which the longitudinal sections extend. The distal section is the section connecting the longitudinal sections. Each of wires 102 is coupled with adjacent ones of wires 102 on either side thereof. Specifically, the longitudinal sections of each of wires 102 are coupled with longitudinal sections of adjacent wires. For example, one longitudinal section of wire 102A is coupled with a longitudinal section of wire 102B, and the other longitudinal section of wire 102A is coupled with a longitudinal section of wire 102C. The other longitudinal section of wire 102B (not coupled with 102A) is coupled with the other longitudinal section of wire 102C (that is also not coupled with 102A). Proximal cap 106 holds the proximal ends of wires 102 together. Extraction string 108 is coupled with wires 102, or with proximal cap 106.

The following paragraphs describe the use of incising implant 100. Thereafter, the components of incising implant 100 would be elaborately described. Incising implant 100 is temporary implanted in the prostatic urethra for creating longitudinal incisions in the inner wall tissues of the prostatic urethra thereby relieving urethra constriction.

Incising implant 100 is implanted by employing a sheath (not shown) for inserting the implant into the urethra. Implant 100 is compressed within the sheath such that the diameter of the circumference of implant 100, illustrated by dotted circle 110, conforms to the inner diameter of the sheath. Wires 102 are made of elastic material, such that when released from the enfolding sheath they regain their original, extended, shape (and the original circumference diameter of implant 100). When positioned in the prostatic urethra, implant 100 is bound by the inner diameter of the urethral walls surrounding it.

Wires 102 push against the surrounding tissues (i.e., apply a radial outward force on the tissues). Over time, the force applied by wires 102 impairs the blood (and oxygen) supply to the tissues in contact with wires 102, thereby inducing tissues necrosis and creating infarcted incisions. Over time, the incisions become deeper until wires 102 reach their full extent (i.e., until implant 100 regains its original circumference diameter as illustrated by dotted circle 110). It is noted however, that implant 100 can be removed before fully regaining its original shape, in case the incisions are determined to be sufficiently deep to relieve the constriction of the urethra, Implant 100 is implanted such that wires 102 are aligned with the longitudinal direction of the urethra. Therefore, wires 102 create longitudinal incisions in the inner wall tissues of the prostatic urethra. That is, the longitudinal incisions are incisions running along the longitudinal axis of the urethra. Put another way, longitudinal incisions are incisions running along (and not across) the urinary passage.

The period of time required for creating incisions that are sufficient to relieve urethra constriction depends on various factors, such as the level of constriction, the materials of wires 102, the original fully extending shape of wires 102, and the like. Implant 100 can remain in the prostatic urethra for a predetermined period of time. Alternatively, implant 100 can remain implanted until the constriction is sufficiently relieved, as determined by a physician, according to tests (e.g., observations of the implant effect over time), or by the subject himself (e.g., according to what the subject feels when urinating). For example, implant 100 can be implanted for a time period ranging between a one hour and several weeks. The incisions created by implant 100 are created over time without causing pain or bleeding to the subject. After implant 100 is implanted, the subject can be released and resume his regular lifestyle, without any hindrances. After the required period of time, implant is removed from the subject.

Incising implant 100 is implanted within the prostatic urethra to relieve constriction of the urethra, caused for example by prostatic enlargement. Implant 100 can be positioned in other, or in additional, areas of the urinal passage, such as the bladder neck. Alternatively, implant 100 can be implanted in any tubular organ that requires relief of a constriction, such as tubular organs of the digestion system, blood vessels, and the like.

Wires 102 (i.e., wires 102A, 102B and 102C) are closed-shaped wires made of elastic material. The material of wires should be elastic enough to allow wires to be compressed within a sheath, and to conform to the inner diameter of the sheath, during insertion into the urethra. The wires should regain their original, extended, shape (and the original circumference diameter) once released from the sheath. Additionally, the wires should be strong enough to apply a force on the surrounding tissues to induce necrosis in the tissues (e.g., a force of 0.5 Newton), and thereby to create infarcted longitudinal incisions. Wires 102 can be made, for example, from Nickel Titanium alloy (Nitinol). Alternatively, implant 100 is made of biodegradable materials, such that there is no need to remove implant 100 from the body of the patient.

The closed shape of wires can be roughly divided into three sections, a proximal section, a middle section consisting of two longitudinal sections, and a distal section (all not referenced). The proximal section (or proximal end) is U-shaped. The longitudinal sections extend from the arms of the U-shaped proximal end and are connected via the distal section (or distal end). The distal section serves as a support crosspiece connecting the longitudinal sections of the wire. Exemplary closed shapes of the wires are illustrated in FIGS. 1A-1C, 2A-2C, 3, and 4.

The longitudinal sections of each of wires 102 are the sections in contact with the surrounding tissues. That is, the longitudinal sections are the sections pushing against the tissues for creating the incisions. The longitudinal sections of each of wires 102 are coupled (i.e., adjoined) with longitudinal sections of adjacent wires. For example, a first lateral section of wire 102A is adjoined with a first longitudinal section of wire 102B, a second longitudinal section of wire 102A is adjoined with a first longitudinal section of wire 102C, and a second longitudinal section of wire 102B is adjoined with a second longitudinal section of wire 102C.

In this manner, the adjoined wires form together a supporting wire frame, such that each closed-shape wire forms a face of the frame, and each adjoined pair of longitudinal sections of adjacent wires forms an edge of the frame.

When the longitudinal sections of wires 102 are pushed against the surrounding tissues (i.e., as implant 100 tries to regain its original shape while being bound by the urethra inner walls), the surrounding tissues apply an opposite force on wires 102 in accordance with the third law of Newton. Each of wires 102 is pushed against the adjacent wires to which it is adjoined. The wire frame increases the structural stability of implant 100 and allowing implant 100 to apply sufficient force for creating the incisions in the surrounding tissues. Thus, the wire frame obviates the need for an additional support element, such as a central support tube.

In the example set forth in FIGS. 1A-1C, wires 102 are adjoined together by being wound (i.e., twisted) around each other. That is, the first longitudinal section of wire 102A and the first longitudinal section of wire 102B are wound around each other; the first second longitudinal section of wire 102A and the first longitudinal section of wire 102C are wound around each other; and the second longitudinal section of wire 102B and the second longitudinal section of wire 102C are wound around each other. The twist coupling of wires 102 further provides structural solidity to implant 100. Thereby, each of wires 102 can be made thinner without compromising the robustness of implant 100. For example, each of wires can be as thin as 0.5 millimeters (i.e., the cross section of each of the wires is 0.5 millimeters).

The wounding of wires 102 can be achieved, for example, by twisting the longitudinal sections around each other and thermally treating implant 100 for stabilizing the winding. Wires 102 can be wound around each other by being placed in a mold having rotating elements that grab the longitudinal sections and wound them around each other.

In the example set forth in FIGS. 1A-C there are three wound wires, each consisting of two longitudinal sections of two adjacent wires, wound around each other. Thus, the wire frame has three longitudinal edges creating three longitudinal incisions. In accordance with an alternative embodiment of the disclosed technique, the implant can include other numbers of closed-shaped wires, such as a single wire, two wires, (for a wire frame of two longitudinal edges creating two longitudinal incisions), four wires (for a wire frame of four lateral edges creating four longitudinal incisions), five wires, and the like.

Proximal cap 106 is coupled with the proximal ends of wires 102 for coupling wires 102 together. Thereby, the wire frame is further strengthened. Put another way, proximal cap 106 helps to maintain the structure of implant 102 (i.e., increases the structural stability) by further adjoining wires 102 to each other.

In the example set forth in FIGS. 1A-1C, proximal cap 106 encases the proximal ends of wires 102. Thereby, proximal cap 106 shields tissues of the urethra from getting caught in the proximal ends of wires 102. Additionally, proximal cap 106 serves to prevent wires 102 from unwinding.

Proximal cap 106 can include a proximal non-round niche (e.g., niche 502 of FIGS. 4A and 4B). The non-round proximal niche of proximal cap 106 is configured to receive a corresponding non-round pin, and to transfer rotary motion of the pin to implant 100. Thereby, the user can rotate implant 100 when implant is located within the bladder of the subject, as would be detailed further herein below with reference to FIGS. 4A-4B and 5A-5L.

Anchoring leaflet 104 serves as a one-way stopper allowing implant to move from the bladder into the prostatic urethra and preventing implant 100 from migrating back toward the bladder by being stuck against one of the urethral sphincters. Leaflet 104 can be a wire leaflet (e.g., as depicted in FIGS. 1A-1C), or any other form allowing it to slice across the urethral sphincters in the proximal direction and preventing it to slide across the urethral sphincters in the distal direction. For example, leaflet can be bar-shaped. Leaflet can be coupled to implant elastically or via an axis, or another coupling mechanism configured to enable leaflet to serve as a one-way stopper for movement across the urethral sphincters. Alternatively, other or additional anchoring elements can be employed for anchoring implant in its place (moving in the proximal direction, the distal direction, or both), such as barbs on wires 102.

Extraction string 108 enables the physician to extract implant 100. Specifically, the distal end of string 108 is coupled with implant 100, and the proximal end of string 108 extends outside of the body of the subject. The physician can insert an extraction sheath into the urethra along string 108 for enfolding implant 100. The physician can extract the enfolded implant by pulling string 108. String 108 is strong enough for pulling implant 100 without being torn (e.g., the thickness and materials of string 108 allow pulling implant 100 via string 108). String 108 can be a single strand or a woven bundle of strands for further fortifying it.

Incising implant 100 is deployed such that it does not extend distally beyond the bladder neck of the subject (i.e., does not extend into the bladder). Specifically, wires 102 do not come into contact with the tissues of the bladder itself. Thereby, implant 100 does not irritate the bladder of the patient.

In accordance with an embodiment of the disclosed technique, the incising implant is colored in such a manner that enables the physician to easily position it in order. For example, the wires of the implant are color coded such that sections that should be positioned on top are colored blue, and sections that should be positioned on the bottom are colored white. The physician can observe the implant in the bladder via a cystoscope, and rotate the implant to the desired orientation according to the colors of the implant.

Figure 2A:
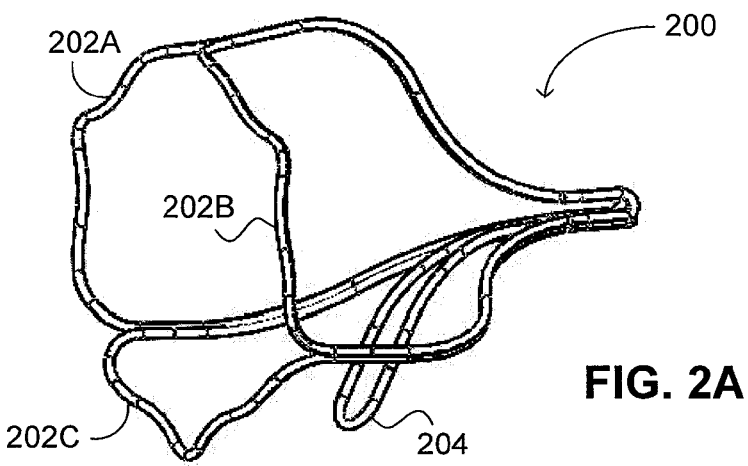
FIGS. 2A, 2B and 2C are schematic illustrations of an incising implant for creating incisions in the inner wall tissues of the prostatic urethra, constructed and operative in accordance with another embodiment of the disclosed technique.
Figure 2B:
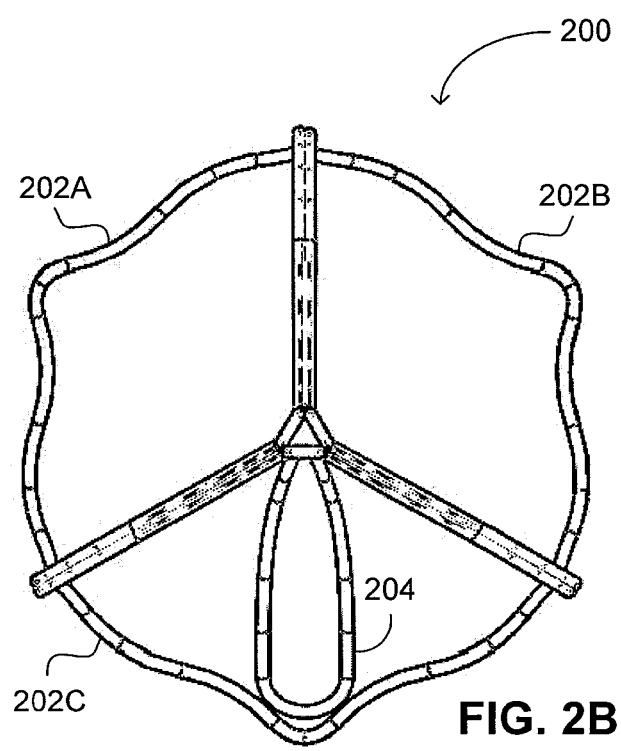
Figure 2C:
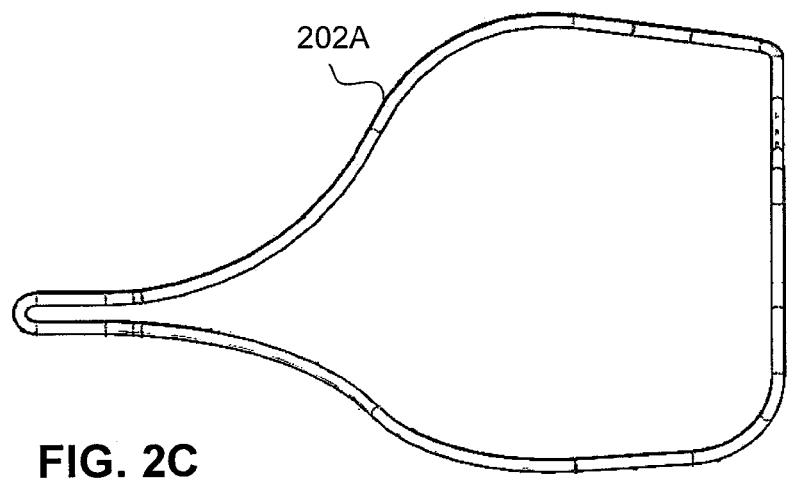

Reference is now made to FIGS. 2A, 2B and 2C, which are schematic illustrations of an incising implant, generally referenced 100, for creating incisions in the inner wall tissues of the prostatic urethra, constructed and operative in accordance with another embodiment of the disclosed technique. FIG. 2A depicts the incising implant from an isometric perspective, FIG. 2B depicts the incising implant from a top-view perspective, and FIG. 2C depicts a closed-shaped wire of the implant, incising implant 200 includes three closed-shaped wires 202A, 202B and 202C (also referred to herein below, together, as wires 202), and an anchoring leaflet 204. The components of implant 200 are similar to those of implant 100, and for the sake of brevity only the differences are elaborated herein below.

The closed shape of each of wires 202 is depicted in FIG. 2C. The closed shape is truncated at the distal end thereof. That is, the distal end of each of wires 202 is substantially perpendicular to the longitudinal axis of implant 200. Thereby, the wires do not come into contact with the tissues of the bladder, for avoiding bladder irritation.

Wires 202 are not wound around each other. Instead, wires 102 can be adjoined to one another (i.e., the longitudinal sections are adjoined to longitudinal sections of adjacent wires) by various manners. For example, the wires are welded together, glued together, or coupled by a coupling mechanism or element (e.g., coupling thread binding the longitudinal sections together).

In the example set forth in FIGS. 2A-2C (and in FIG. 3 herein below), the incising implant is depicted without a proximal cap and an extraction string. It is noted however, that the implant can include any of the proximal cap, the extraction string, or both.

Reference is now made to FIG. 3, which is a schematic illustration of an incising implant generally referenced 300, for creating incisions in the inner wall tissues of the prostatic urethra, constructed and operative in accordance with a further embodiment of the disclosed technique. Incising implant 300 includes three closed-shaped wires 302A, 302B and 302C (also referred to herein below, together, as wires 302) and an anchoring leaflet 306. The components of implant 300 are similar to those of implant 100, and for the sake of brevity only the differences are elaborated herein below. Implant 300 is depicted from a bottom-view perspective (i.e., as seen by a proximally located observer). The closed shape of wires 302 is triangular, such that together wires 302 form a triangular-pyramid wire frame with the proximal ends of the wires forming the apex of the pyramid, and the distal ends forming the base of the pyramid. The adjoined longitudinal sections of wires 302 form the longitudinal edges of the triangular pyramid.

Reference is now made to FIGS. 4A and 4B, which are schematic illustrations of a proximal niche, generally referenced 402, of a proximal cap of an incising implant, constructed and operative in accordance with yet another embodiment of the disclosed technique. The proximal cap is detailed herein above with reference to proximal cap 106 of FIGS. 1A-1C. The niche has a non-round shape for allowing it to transfer rotary motion from the corresponding pin inserted into the niche. Thereby, the physician can rotate the incising implant from afar (e.g., when the implant is in the bladder). In the example set forth in FIG. 4A, the shape of niche 402 is rectangular, and in the example set forth in FIG. 4B, the shape of niche 402 is hexagonal. Alternatively, the niche can have any shape allowing it to transfer rotary motion (i.e., rotations around the central axis of the proximal cap), such as non-round shapes, a slit, an array of niches (e.g., two holes), and the like.

Figure 5A:
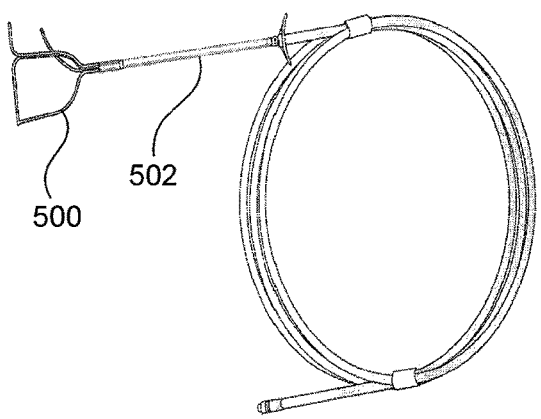
FIGS. 5A-5L are schematic illustrations of a method for deploying and for extracting an incising implant, operative in accordance with yet a further embodiment of the disclosed technique.

Reference is now made to FIGS. 5A-5L, which are schematic illustrations of a method for deploying and for extracting an incising implant, operative in accordance with yet a further embodiment of the disclosed technique. With reference to FIG. 5A, an extraction string 510 (shown in FIG. 5J) extends from the proximal end of implant 500. Implant 500 includes a proximal cap having a non-round proximal niche (both not shown). A guidewire 506 includes a distal head (i.e., distal pin), which shape corresponds to the proximal niche of the proximal cap of implant 500; and an inner channel (not show). The distal head of guidewire 508 is inserted into the proximal niche of the proximal cap of implant 500. Extraction string 510 runs through the inner channel of guidewire 506. At the proximal end of extraction string 510 a proximal knot 512 (shown in FIG. 5J) holds guidewire 506 attached to implant 500. Incising implant 500 is attached to the distal and of deployment sheath 502, such that guidewire 508 (and extraction string 510 running therethrough) runs through sheath 502.

Figure 5B:
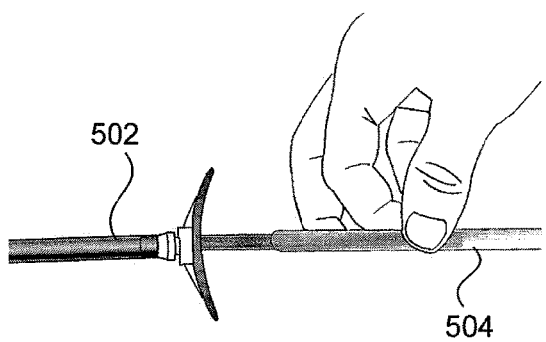
Figure 5C:
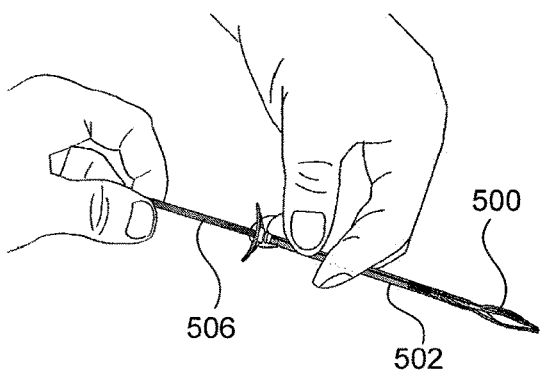

With reference to FIG. 5B, a physician removes protective cover 504 from implant 500, thereby implant 500 expands to its original open configuration (as seen in any of drawings 1A-1C, 2A-2C, and 3). A protective cover 504 keeps implant 500 sterile during storage prior to use. With reference to FIG. 5C, while holding guidewire 506, the physician pushes sheath 502 over implant 500 thereby enfolding implant 500 within sheath 502 for delivery into the urethra.

Figure 5D:
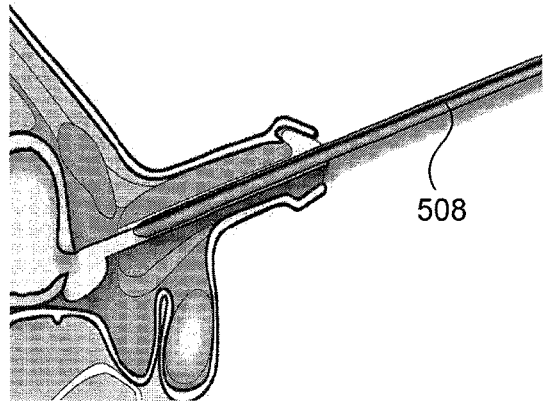
Figure 5E:
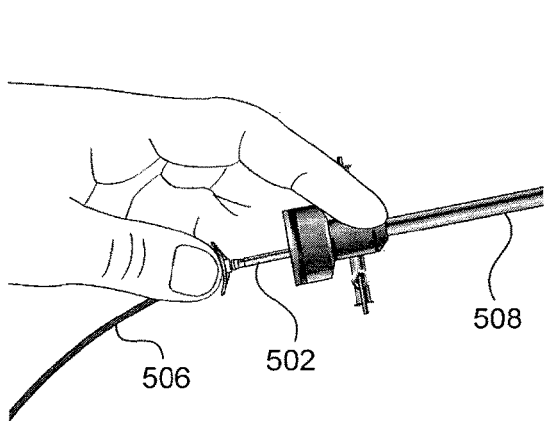
Figure 5F:
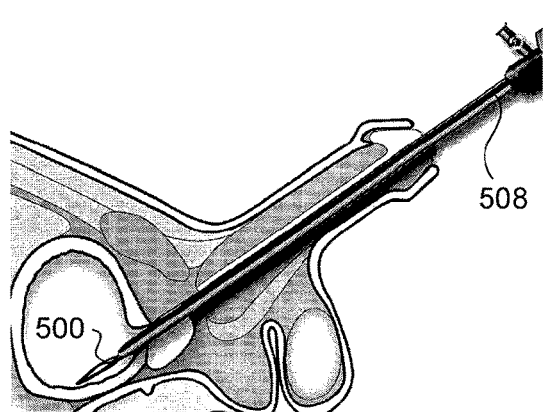
Figure 5G:
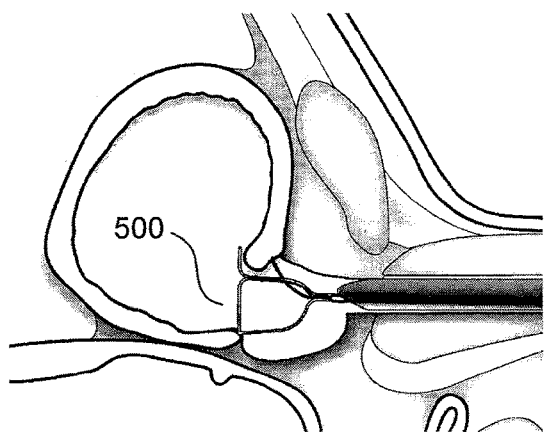

With reference to FIG. 5D, the physician inserts a rigid cystoscope 508 (e.g., size 20 French) into the urethra, for example, as in a routine urethral catheterization procedure. With reference to FIG. 5E, the physician Inserts sheath 502, including compressed implant 500 therewithal, into cystoscope 508. The physician continues pushing implant 500 through cystoscope 508 by pushing guidewire 506, until implant 500 extends through the distal end of cystoscope 508. With reference to FIG. 5F, the physician removes sheath 502 from implant 500 and out of cystoscope 508. With reference to FIG. 5G, once released from sheath 502 and from cystoscope 508, implant 500 expands (i.e., regains its original extended shape).

Figure 5H:
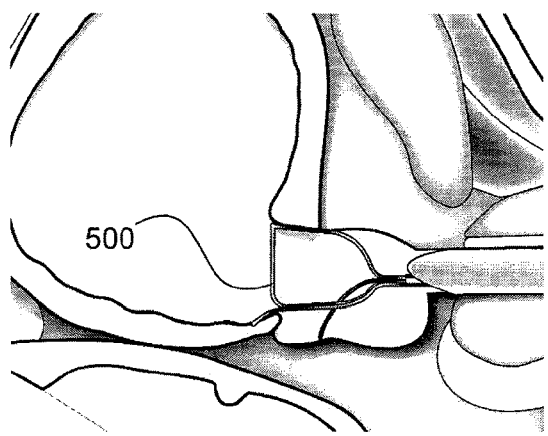

With reference to FIG. 5H, the physician rotates implant 500 to the desired orientation by rotating guidewire 506 (and its distal head inserted into the proximal niche of implant 500). An anchoring leaflet of implant 500 (e.g., leaflet 104 of FIGS. 1A-1C) should be positioned posteriorly. The wires of implant 500 can be color coded, such that the sections that should be positioned on the top are colored, for example, blue; and the sections that should be positioned on the bottom are colored, for example, white. The physician rotates implant as detailed further herein above with reference to proximal cap 106 of FIGS. 1A-1C, and proximal cap 400 of FIGS. 4A-4B.

Figure 5I:
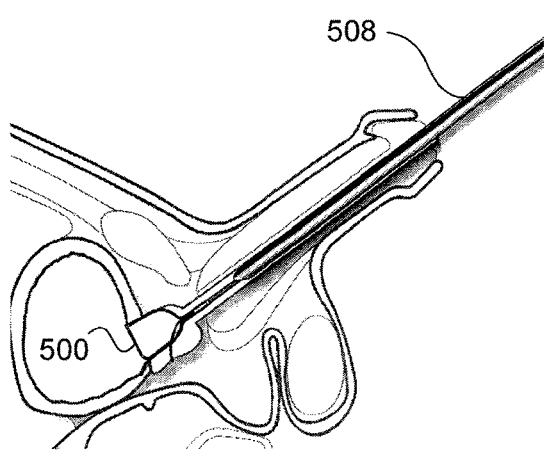
Figure 5J:
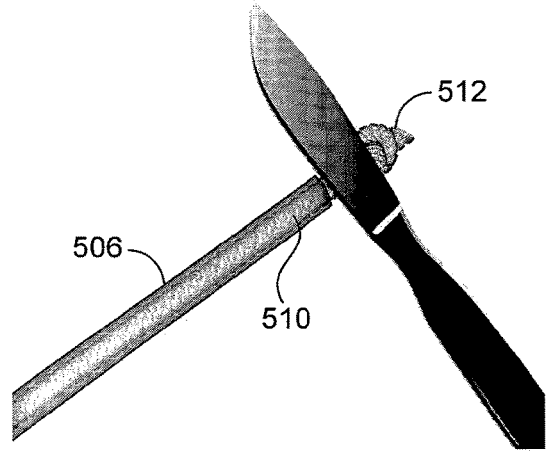

With reference to FIG. 5I, while holding implant 500 in place by using guide wire 506, the physician retracts cystoscope 508. Thereafter, the physician pulls implant 500 via grade wire 506 until the anchoring leaflet of implant 500 slides over a urethral sphincter and implant is positioned within the prostatic urethra. With reference to FIG. 5J, the physician cuts knot 512 at the proximal end of extraction string 510, and retracts guidewire 506 from the urethra.

Thereby, implant 500 is implanted within the prostatic urethra and starts applying radial outward force on the surrounding tissues of the inner walls of the urethra for creating longitudinal incisions. Implant 500 is left within the prostatic urethra for a selected time period (e.g., ranging between one hour and several weeks. Thereafter implant 500 is removed as would be detailed below. Alternatively, implant 500 is made of biodegradable materials and simply dissolves after a selected time period.

Figure 5K:
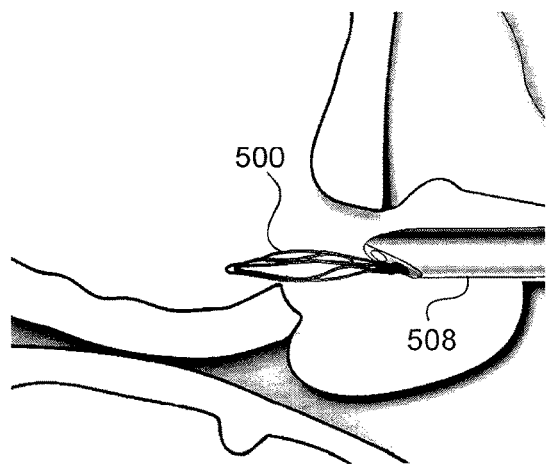
Figure 5L:
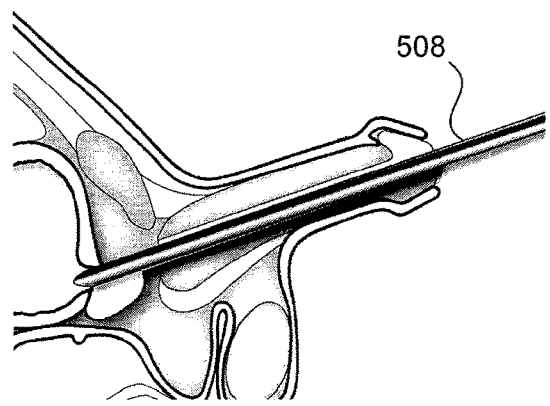

With reference to FIG. 5K, the physician inserts cystoscope 508 through the urethra toward implant 500 over extraction string 510. Alternatively, the physician can insert sheath 502 instead of cystoscope 508. The physician pushes cystoscope 508 until if enfolds implant 500. With reference to FIG. 5L, the physician extracts implant 600 enfolded within cystoscope 508 by pulling implant via extraction string 510. Then, the physician extracts cystoscope 508 from the urethra.

It will be appreciated by persons skilled in the art that the disclosed technique is not limited to what has been particularly shown and described hereinabove. Rather the scope of the disclosed technique is defined only by the claims, which follow.

The invention claimed is:

1. An incising implant for the prostatic urethra of a subject, the incising implant comprising:
   at least two wires, the at least two wires comprising closed-shaped wires, each of said wires having a proximal section, a distal section and a plurality of longitudinal sections extending along a length between said proximal section and said distal section, each of said wires being elastic thereby being compressible into a compressed configuration, said longitudinal sections of each of said wires being adjoined with another longitudinal section of another one of said wires along said length, in an open configuration of said incising implant to allow said incising implant to incise tissue in said prostatic urethra, said at least two wires diverge at the distal sections so that said distal sections form a simple closed curve shape at a terminus of said incising implant in said open configuration; and
   an anchor, said anchor being closed-shaped and extending outwardly from at least one of said proximal sections and through one of said closed-shaped wires in said open configuration.

2. The incising implant of claim 1, wherein each of said longitudinal sections of each of said wires being wound around said another longitudinal section of said another one of said wires.

3. The incising implant of claim 1, further comprising a proximal cap coupled with said proximal section of each of said wires, said proximal cap configured to hold said wires together.

4. The incising implant of claim 3, wherein said proximal cap including a proximal non-round niche configured to accept a corresponding pin, and configured to transfer rotary motion of said pin to said incising implant.

5. The incising implant of claim 3, configured to be used with a guidewire configured for insertion into a proximal niche of said proximal cap of said incising implant.

6. The incising implant of claim 1, further comprising an extraction string configured to couple with said incising implant, said extraction string being arranged to allow pulling said incising implant out of said subject.

7. The incising implant of claim 1, wherein said anchor is configured for preventing said incising implant from moving toward a bladder of said subject.

8. The incising implant of claim 1, wherein said wires form together a wire frame having a proximal apex formed by said proximal section of each of said wires, and having a distal base formed by said distal ends of each of said wires.

9. The incising implant of claim 1, wherein said wires are selected from a list consisting of: Nickel Titanium alloy (Nitinol), and biodegradable materials.

10. The incising implant of claim 1, wherein said distal sections of said wires forms form a triangular shape.

11. The incising implant of claim 1, wherein said incising implant is enfolded in a sheath in said compressed configuration.

12. An implant for the prostatic urethra of a subject, the implant comprising:
   at least two wires being closed-shaped wires, each wire having a proximal section, a distal section and a plurality of longitudinal sections extending between said proximal section and said distal section, each of said wires being elastic thereby being compressible into a compressed configuration, at least one longitudinal section of each of said wires being at least partially adjoined with another longitudinal section of another one of said wires, said closed-shaped wires diverge from each other at distal ends of the closed-shaped wires in an open configuration of said implant; and
   an anchor, said anchor including at least two anchor sections, said at least two anchor sections being distinct from said at least two wires, said at least two anchor sections are coupled with said proximal section of said closed-shaped wires, at least one anchor section extends from said proximal section of one of said at least two wires, and at least another anchor section extends from said proximal section of another one of said at least two wires, said at least two anchor sections extending outwardly and being united together in a termination of said anchor;

wherein said implant is implantable in said prosthetic urethra of said subject, said wires are configured for applying pressure on surrounding tissues of said prosthetic urethra in said open configuration of said implant.

13. The implant of claim 12, each of said longitudinal sections of each of said wires being wound around said another longitudinal section of said another one of said wires.

14. The implant of claim 12, wherein the anchor is configured for preventing said implant from moving in the direction of a bladder of said subject.

15. The implant of claim 12, further comprising another anchor configured to anchor said implant from movement in either one of a proximal direction or a distal direction.

16. The implant of claim 12, wherein each adjoined pair of said longitudinal sections of said wires forms an edge of a frame of said wires in a longitudinal direction.

\* \* \* \* \*